(12) United States Patent
Challener et al.

(10) Patent No.: US 6,625,336 B2
(45) Date of Patent: Sep. 23, 2003

(54) OPTICAL SENSOR HAVING DIELECTRIC FILM STACK

(75) Inventors: William A. Challener, Grant, MN (US); James M. DePuydt, Stillwater, MN (US); William A. Tolbert, Woodbury, MN (US)

(73) Assignee: Imation Corp., Oakdale, MN (US)

( * ) Notice: Subject to any disclaimer, the term of this patent is extended or adjusted under 35 U.S.C. 154(b) by 0 days.

(21) Appl. No.: 09/967,019

(22) Filed: Sep. 28, 2001

(65) Prior Publication Data

US 2002/0018610 A1 Feb. 14, 2002

Related U.S. Application Data

(62) Division of application No. 09/174,178, filed on Oct. 16, 1998.

(51) Int. Cl.[7] .................................................. G02B 6/00
(52) U.S. Cl. ........................................ 385/12; 385/131
(58) Field of Search ...................... 385/12, 13, 11–129, 385/130, 131; 356/445; 436/527

(56) References Cited

U.S. PATENT DOCUMENTS

| 4,828,387 A | 5/1989 | Sawyers et al. |
| 4,877,747 A | 10/1989 | Stewart |

(List continued on next page.)

FOREIGN PATENT DOCUMENTS

| CA | 2108705 | 5/1994 |
| EP | 0 321 523 B1 | 12/1992 |
| EP | 0 517 930 A1 | 12/1992 |
| EP | 0 677 734 A2 | 10/1995 |
| WO | 90/08318 | 7/1990 |
| WO | WO 92/04617 | 3/1992 |
| WO | WO 95/33198 | 12/1995 |
| WO | WO 97/09608 | 3/1997 |
| WO | WO 97/29362 | 8/1997 |
| WO | WO 98/22807 | 5/1998 |
| WO | WO 00/05582 | 2/2000 |

OTHER PUBLICATIONS

"Unusual splitting behavior of the dispersion of surface polaritons in gratings of different symmetry, amplitude, and profile," Fischer et al., *Applied Optics*, vol. 34, No. 25, Sep. 1, 1995, pp. 5773–5779.

(List continued on next page.)

*Primary Examiner*—Ellen E. Kim
(74) *Attorney, Agent, or Firm*—Eric D. Levinson

(57) ABSTRACT

A method and apparatus for optically assaying a targeted substance in a sample using a sensor comprising a dielectric film stack having a plurality of dielectric layers. For at least one angle of incidence the dielectric layers operate as a waveguide for light incident upon the sensor. In one configuration, each dielectric layer comprises a dielectric material selected from a first dielectric material having a first index of refraction and a second dielectric material having a second index of refraction. The dielectric film stack is formed such that the dielectric material of the dielectric layers alternates between the first dielectric material and the second dielectric material. The dielectric film stack is either formed as a dielectric mirror such that light incident upon the sensor reflects from the sensor or as an anti-reflection film stack such that light incident upon the light beam propagates through the sensor. The inventive sensor exhibits a resonance that is comparable in magnitude with resonances commonly exhibited by conventional SPR sensors. However, unlike grating-based SPR sensors, the inventive sensor allows a sample to be assayed with substrate-incident light such that the incident light need not propagate through the sample. In addition, because the sensor does not rely on the use of conductive metals, the sensor enables sharp resonances at shorter wavelengths than conventional SPR sensors.

16 Claims, 4 Drawing Sheets

U.S. PATENT DOCUMENTS

| | | | |
|---|---|---|---|
| 4,880,752 A | | 11/1989 | Keck et al. |
| 4,882,288 A | | 11/1989 | North et al. |
| 4,931,384 A | | 6/1990 | Layton et al. |
| 4,992,385 A | | 2/1991 | Godfrey |
| 5,035,863 A | | 7/1991 | Finlan et al. |
| 5,071,248 A | | 12/1991 | Tiefenthaler et al. |
| 5,118,608 A | | 6/1992 | Layton et al. |
| 5,310,686 A | | 5/1994 | Sawyers et al. |
| 5,341,215 A | * | 8/1994 | Seher .......................... 356/445 |
| 5,365,067 A | | 11/1994 | Cole et al. |
| 5,455,178 A | | 10/1995 | Fattinger |
| 5,478,755 A | | 12/1995 | Attridge et al. |
| 5,479,260 A | | 12/1995 | Fattinger |
| 5,492,840 A | | 2/1996 | Malmqvist et al. |
| 5,583,643 A | | 12/1996 | Gass et al. |
| 5,598,267 A | | 1/1997 | Sambles et al. |
| 5,606,633 A | * | 2/1997 | Groger et al. ................. 385/11 |
| 5,636,633 A | | 6/1997 | Messerschmidt et al. |
| 5,738,825 A | | 4/1998 | Rudigier et al. |
| 5,751,482 A | | 5/1998 | Challener, IV |
| 5,776,785 A | | 7/1998 | Lin et al. |
| 5,846,843 A | * | 12/1998 | Simon .......................... 385/12 |
| 5,892,577 A | | 4/1999 | Gordon |
| 5,925,878 A | | 7/1999 | Challener |
| 5,955,378 A | | 9/1999 | Challener |
| 5,986,762 A | | 11/1999 | Challener |
| 5,991,488 A | * | 11/1999 | Salamon et al. .............. 385/11 |
| 5,994,150 A | | 11/1999 | Challener et al. |
| 6,320,991 B1 | * | 11/2001 | Challener et al. ............. 385/12 |

OTHER PUBLICATIONS

"A Compact Surface Plasmon Resonance Sensor for Measurement of Water in Process," K. Matsubara et al., *Applied Spectroscopy*, vol. 42, No. 8, 1988, pp. 1375–1377, 79) No month.

"Detection of Immuno–complex Formation via Surface Plasmon Resonance on Gold–coated Diffraction Gratings," Cullen et al., *Biosensors*, 3, 1987/88, pp. 211–225, No month.

"Grating–Coupled Surface Plasmon for Measuring the Refractive Index of a Liquid Sample," Kano et al., *J. Phys. D: Applied Physics*, vol. 34, Jan. 1995, pp. 331–335.

"Polarisation conversion through the excitation of surface plasmons on a metallic grating," Bryan–Brown et al., *Journal of Modern Optics*, Jan. 1990, vol. 37, No. 7, pp. 1227–1232.

"Resonance anomalies in the light intensity reflected at silver gratings with dielectric coatings," Pockrand, *J. Phys. D: Appl. Phys.*, vol. 9, May 1976, pp. 2423–2432.

"Surface–resonance polarization conversion mediated by broken surface symmetry," Elston et al., *Physical Review B*, vol. 44, No. 7, Aug. 15, 1991, pp. 3483–3485.

"Gas Detection by Means of Surface Plasmon Resonance," Nylander et al., *Sensors and Actuators*, 3, 1982/83, pp. 79–88, No month.

A Direct Surface Plasmon–Polariton Immunosensor: Preliminary Investigation of the Non–specific Adsorption of Serum Components to the Sensor Interface, Cullen et al., *Sensors and Actuators*, B1 (1990), pp. 576–579, No month.

"Surface plasmon resonance on gratings as a novel means for gas sensing," Vukusic et al., *Sensors and Actuators, B–8*, 1992, 155–160, No month.

"Development of a prototype gas sensor using surface plasmon resonance on gratings," Jory et al., *Sensors and Actuators B*, 17, 1994, pp. 203–209, No month.

"Double excitation of a resonant surface plasmon maximum," Jory et al., *Journal of Modern Optics*, vol. 40, No. 9, 1993, pp. 1657–1662, No month.

"Choice of metal and wavelength for surface–plasmon resonance sensors: some considerations," Brujin et al., *Applied Optics*, vol. 31, No. 4, Feb. 1, 1992, pp. 440–442.

"Optimization of a chemooptical surface plasmon resonance based sensor," Gent et al., *Applied Optics*, vol. 29, No. 19, Jul. 1, 1990, pp. 2843–2849.

Detection of Amine Gases by Color Changes of Acid–Base Indicators Supported on Inorganic Films, Takao et al., *Reports of the Faculty of Engineering Nagasaki University*, vol. 26, No. 46, Jan. 1996, pp. 105–111, in Japanese with English Abstract.

"Properties and applications of layered grating resonances," Gallatin, *SPIE, Application and Theory of Periodic Structures, Diffraction Gratings, and Moire Phenomena III*, vol. 815, 1987, pp. 158–167, No month.

"Vector diffraction of a grating with conformal thin films," Challener, *Optical Society of America*, vol. 13, No. 9, Sep. 1996, pp. 1859–1869.

"Thin–film optical filters with diffractive elements and waveguides," Shin et al., *Optical Engineering*, vol. 37, No. 9, Sep. 1998, pp. 2634–2646.

"Grating couplers as chemical sensors: a new optical configuration," Brandenburg et al., *Sensors and Actuators B*, 17, 1993, pp. 35–40, No month.

"Surface Plasmon Resonance (SPR) for Biosensing," Chapter 7, Lawrence et al., pp. 149–168, "Monitoring Immunoreactions with SPR," Chapter 16, Geddes et al., pp. 349–368, *Handbook for Biosensors and Electronic Noses, Medicine, Food, and the Environment*, CRC Press, Inc., 1997, No month.

* cited by examiner

OPTICAL SENSOR HAVING DIELECTRIC FILM STACK

This a divisional of application Ser. No. 09/174,178, filed Oct. 16, 1998.

FIELD OF THE INVENTION

This invention relates generally to the field of optical assaying, and more particularly to an optical sensor having a dielectric film stack.

BACKGROUND OF THE INVENTION

Extremely sensitive optical sensors have been constructed by exploiting an effect known as surface plasmon resonance (SPR). These sensors are capable of detecting the presence of a wide variety of materials in concentrations as low as picomoles per liter. SPR sensors have been constructed to detect many biomolecules including keyhole limpet hemocyanin, α-fetoprotein, IgE, IgG, bovine and human serum albumin, glucose, urea, avidin, lectin, DNA, RNA, HIV antibodies, human transferrin, and chymotrypsinogen. Additionally, SPR sensors have been built which detect chemicals such as polyazulene and nitrobenzenes and various gases such as halothane, trichloroethane and carbon tetrachloride.

An SPR sensor is constructed by sensitizing a surface of a substrate to a specific substance. Typically, the surface of the substrate is coated with a thin film of metal such as silver, gold or aluminum. Next, a monomolecular layer of sensitizing material, such as complementary antigens, is covalently bonded to the surface of the thin film. In this manner, the thin film is capable of interacting with a predetermined chemical, biochemical or biological substance. When an SPR sensor is exposed to a sample that includes a targeted substance, the substance attaches to the sensitizing material and changes the effective index of refraction at the surface of the sensor. Detection of the targeted substance is accomplished by observing the optical properties of the surface of the SPR sensor.

There are two common constructions of an SPR sensor. FIG. 1 illustrates a prism-based SPR sensor 10 that is the most common form of SPR sensors. Sensor 10 includes a disposable slide 20 that is placed on a fixed glass prism 12. Slide 20 is coated with a metal film 16 and sensitizing material 22 is capable of interacting with target substance 18 in sample 21. Before placing slide 20 on prism 12, an operator coats prism 12 with an anti-reflection coating 14, often a fluid, in order to prevent light beam 24 from reflecting before reaching metal-film layer 16.

Light source 28 generates light beam 24 that is incident upon sensor 10. Sensor 10 reflects light beam 24 as light beam 26 received by detector 30. At a specific angle of incidence of light beam 24, known as the resonance angle, a very efficient energy transfer and excitation of the surface plasmon occurs in metal film 16. As a result, reflected light 26 exhibits an anomaly, such as a sharp attenuation, and the resonance angle of sensor 10 can be readily detected. When targeted substance 18 attaches to sensitizing material 22, a shift in the resonance angle occurs due to the change in the refractive index at the surface of sensor 10. A quantitative measure of the concentration of targeted substance 18 can be calculated according to the magnitude of shift in the resonance angle.

A second common form of an SPR sensor, known as grating-based SPR sensor, involves the use of a metal diffraction grating instead of glass prism. FIG. 2 illustrates a grating-based SPR sensor 40 in which substrate 45 is formed to have sinusoidal grooves. In grating-based SPR sensors, the period of the groove profile of substrate 45 typically ranges from 0.4 micrometers to 2.0 micrometers. Thin metal film 42 is formed outwardly from the surface of substrate 45 and comprises any suitable metal such as aluminum, gold or silver. In one embodiment, layer 42 comprises silver having a thickness of approximately 100 nm.

Sensitizing layer 44 is formed outwardly from metal film 42. Sensitizing layer 44 is selected to interact with a predetermined chemical, biochemical or biological substance 18 contained in sample 21. In one embodiment, sensitizing layer 44 comprises a layer of antigens capable of trapping a complementary antibody. Recently, several techniques have been developed for attaching antigens as a receptive material to film 42 such as spin coating with a porous silica sol-gel or a hydrogel matrix. Preferably, sensitizing layer 44 is less than 100 nm thick.

In FIG. 2, light source 28 produces light beam 24 incident upon sensor 40 such that detector 30 receives reflected light beam 26. For grating-based SPR sensors, resonance occurs, and reflected light beam 26 exhibits an anomaly, when a polarization component of light beam 24 is perpendicular to the groove direction of the surface of substrate 45 and the angle of incidence of light beam 24 is appropriate for energy transfer and excitation of the surface plasmon in thin metal film 42.

Grating-based SPR sensors have several distinct advantages over prism-based SPR sensors. For example, the resonance angles of grating-based SPR sensors may be finely tuned by adjusting the groove profile. In addition, grating-based SPR sensors do not require the use of an anti-reflection coating. Grating-based SPR sensors, however, suffer from the fact that the light must propagate through the sample as opposed to prism-based sensors in which the incident light propagates through the prism and strikes the metal film opposite from the sample. Propagation through the sample is disadvantageous because the sample tends to absorb or scatter the incident light. For these reasons, grating-based SPR sensors are ill suited for assaying liquids, such as blood, and are primarily used in gas sensing applications. Furthermore, both of the above-described SPR sensors rely on a highly conducting metallic film to support the surface plasmon resonance. This metal film, however, limits the wavelength of the resonance to the red or infrared region of the light spectrum because at shorter wavelengths the conductivity of even the best metals is not sufficient to generate sharp resonances, thereby resulting in lower sensitivity.

For the reasons stated above, and for other reasons stated below which will become apparent to those skilled in the art upon understanding the present invention, there is a need in the art for an optical sensor having the benefits of grating-based SPR sensor that does not require that the incident light propagate through the sample.

SUMMARY OF THE INVENTION

Described herein is a method and apparatus for optically assaying a targeted substance in a sample using an inventive sensor that overcomes the above-described deficiencies of conventional grating-based and prism-based SPR sensors. The sensor exhibits a sharp resonance that is comparable in magnitude with resonances commonly exhibited by conventional SPR sensors. However, unlike grating-based SPR sensors, a sample may be assayed by reflectance from the substrate side without propagating light through the sample. In addition, the sensor allows a sample to be assayed with transmitted light. One advantage of assaying with transmitted light is the ability to use a diffused light source. Because the sensor does not rely on the use of conductive metals, the sensor enables sharp resonances at shorter wavelengths than conventional SPR sensors.

According to one aspect, the invention is a sensor comprising a dielectric film stack having a plurality of dielectric layers. The dielectric layers operate as a waveguide such that a portion of the incident light propagates within the dielectric film stack for at least one angle of incidence. In one embodiment, the dielectric layers are formed with a dielectric material selected from either a first dielectric material having a first index of refraction or a second dielectric material having a second index of refraction. In one configuration, the dielectric film stack is formed such that the dielectric material of the dielectric layers alternates between the first dielectric material and the second dielectric material. The dielectric film stack may be formed as a dielectric mirror, such that light incident upon the sensor substantially reflects from the sensor, or as an anti-reflection film stack such that incident light is transmitted through the sensor with substantially no reflection.

According to another aspect, the invention is a sensing system including a sensor having a stack of dielectric layers. A light source exposes the sensor with a light beam. The dielectric layers of the sensor operate as a waveguide such that a portion of the incident light propagates within the dielectric film stack for at least one angle of incidence. A detector receives light from the sensor and produces an output signal representative of an intensity of the received light. A controller is coupled to the detector and calculates a measure of the substance in the sample as a function of the output signal. In one embodiment a diffuser diffuses the incident light beam from the light source and a lens focuses the light transmitted through the sensor onto a corresponding element of the detector array according to a transmission angle.

According to yet another aspect, the invention is a method for assaying a targeted substance in a sample. A sensor is interacted with the sample having a targeted substance. The sensor comprises a dielectric film stack having a plurality of dielectric layers that operate as a waveguide for incident light. A measure of the targeted substance in the sample is determined as a function of a shift in a detected optical anomaly exhibited by light received from the sensor. In one embodiment, the measure is determined by detecting an optical anomaly in light reflected by the sensor. In another embodiment, the measure includes detecting an optical anomaly in light transmitted through the sensor.

These and other features and advantages of the invention will become apparent from the following description of the preferred embodiments of the invention.

DETAILED DESCRIPTION

In the following detailed description, references are made to the accompanying drawings that illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

Figure 1:
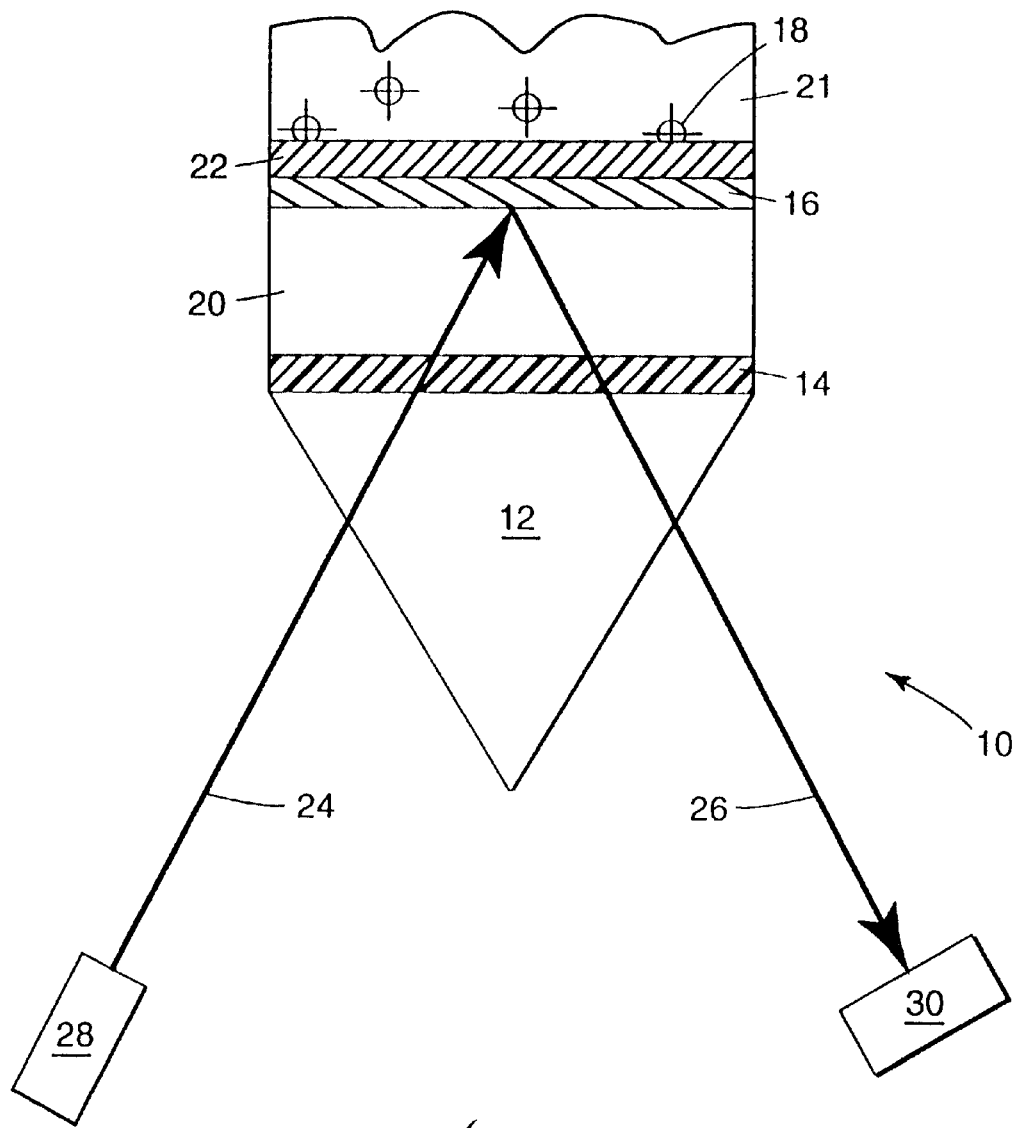
FIG. 1 is a schematic side view of a sensing system having a prism-based surface plasmon resonance sensor.
Figure 2:
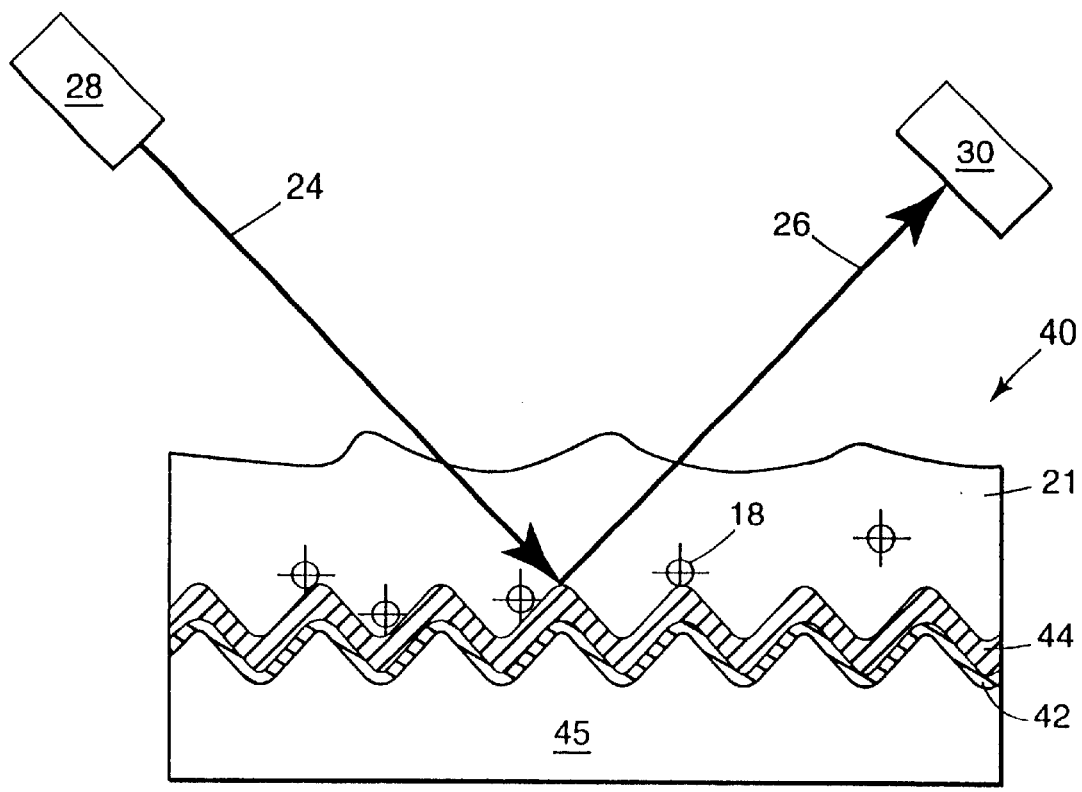
FIG. 2 is a schematic side view of a sensing system having a grating-based surface plasmon resonance sensor.
Figure 3:
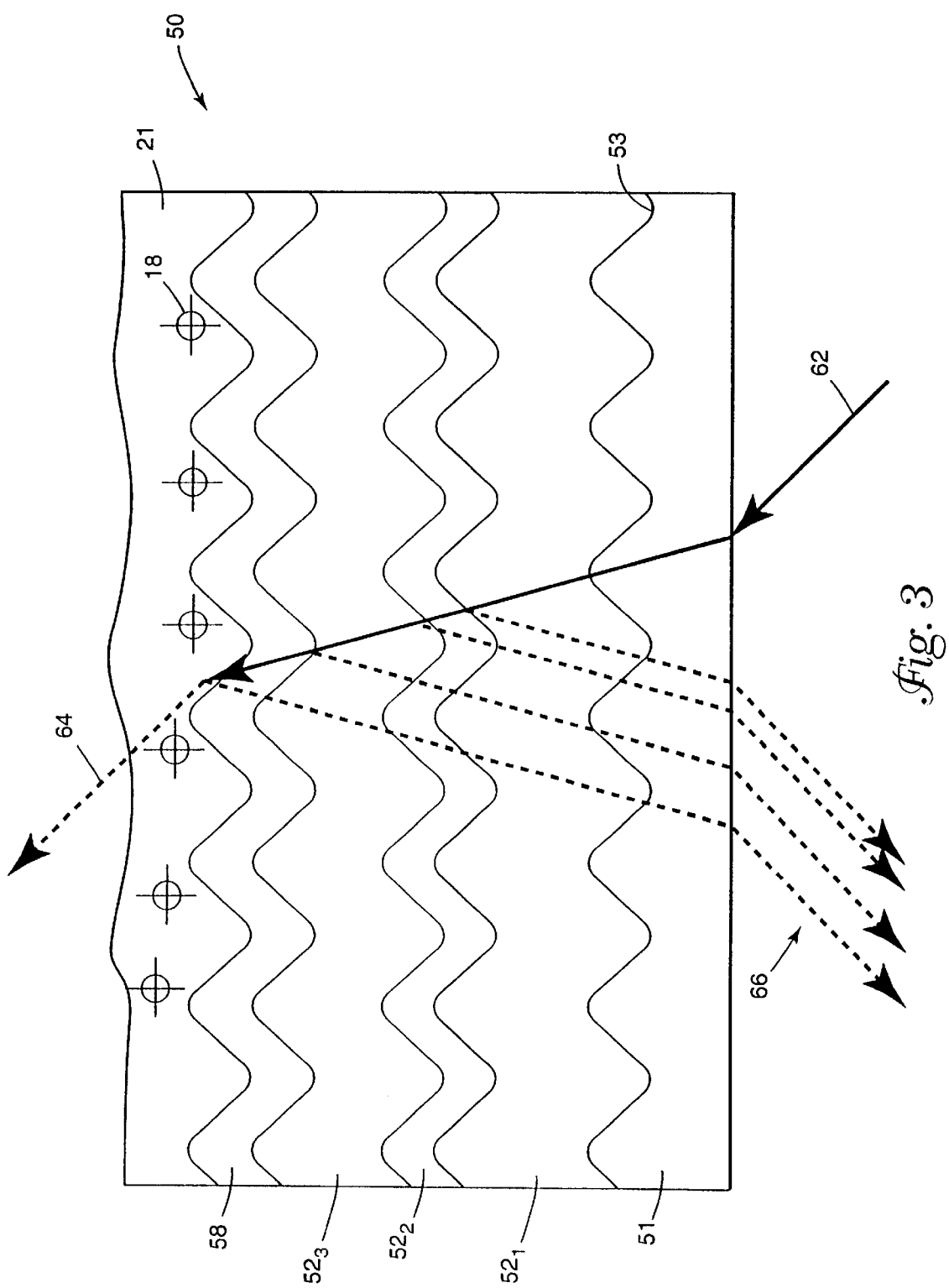
FIG. 3 is a cross-sectional view of one embodiment of an optical sensor having a dielectric film stack in accordance with the present invention.

FIG. 3 is a cross-sectional profile of an optical sensor 50 formed in accordance to the present invention. It is observed that an optical sensor may be constructed which exhibits resonance angles comparable to conventional SPR sensors but which overcomes many of the above-described disadvantages. More specifically, the inventive sensor 50 uses a dielectric film stack instead of a thin metal film. Sensor 50 includes substrate 51 having surface 53 formed with sinusoidal grooves. The period of the groove profile of surface 53 may range from less than 0.4 micrometers to over 2.0 micrometers. Other groove profiles, such as trapezoidal, square, etc., are also well suited for the invention.

Formed outwardly from surface 53 of substrate 51 is a plurality of transparent dielectric layers 52 that collectively form a dielectric film stack on surface 53 of substrate 51. Although illustrated as such, dielectric layers 52 need not conform to the surface profile of substrate 51. As described in detail below, sensor 50 exhibits sharp resonances that are comparable in magnitude with resonances commonly seen in SPR sensors. In one embodiment, dielectric layers 52 of the dielectric film stack are configured to operate as a dielectric mirror that reflects substantially all of light beam 62 at non-resonance angles. More specifically, each dielectric layer 52 of the dielectric film stack reflects a portion of light beam 62 as light beam 66. This embodiment is advantageous because, unlike grating-based SPR sensors, sample 21 may be assayed using substrate-incident light beam 62 such that the light beam 62 need not propagate through sample 21. In another embodiment, sensor 50 is not constructed as a dielectric mirror but as an anti-reflection film stack. In this configuration, at non-resonance angles light beam 62 transmits through sensor 50 with substantially no diffusion or reflection and emerges as light beam 64. In this manner, the dielectric film stack of sensor 50 operates exactly opposite when it is formed as an anti-reflection dielectric film stack than when it is formed as a dielectric mirror. Configuration of the dielectric film stack for operation as either a dielectric mirror or as an anti-reflection film stack is discussed in detail below.

Regardless of whether the dielectric film stack is configured to operate as a dielectric mirror or an anti-reflection film stack, at the resonance angles the dielectric film stack operates as a waveguide such that reflected light beam 66 and transmitted light beam 64 exhibit sharp anomalies. At the resonance angles energy is transferred from light beam 62 to dielectric layers 52 of the dielectric film stack such that dielectric layers 52 collectively act as a waveguide. When dielectric layers 52 collectively operate as a waveguide a finite portion of incident light beam 62 propagates within the dielectric film stack. If the dielectric film stack is constructed as a dielectric mirror, the remaining light not propagating within the dielectric film stack transmits through sensor 50 and emerges as light beam 64, thereby causing a sharp attenuation in reflected light 66 and a sharp increase in transmitted light 64. If, however, the dielectric film stack is constructed as an anti-reflection film stack, the remaining light is reflected as light beam 66, thereby causing a sharp attenuation in transmitted light 64 and a sharp increase in reflected light 66.

Sensitizing layer 58 is formed outwardly from outermost dielectric layer 52 and is selected to interact with a predetermined chemical, biochemical or biological substance 18 contained in sample 21. When targeted substance 18 attaches to sensitizing layer 58, a shift in the resonance angles occurs due to the change in the refractive index of sensor 50. A quantitative measure of the concentration of targeted substance 18 can be calculated according to the magnitude of shift in the resonance angle by monitoring either reflected light 66 or transmitted light 64. Thus, one advantage of sensor 50 over conventional SPR sensors is that sensor 50 can be used in reflection-based sensing systems or transmission-based sensing systems.

In one embodiment the dielectric film stack is configured to operate as a dielectric mirror by forming each dielectric layer with a dielectric material selected from a first dielectric material and a second dielectric material. The first dielectric material has a first index of refraction while the second dielectric material has a second index of refraction. In one particularly advantageous configuration, the stack of dielectric layers is formed such that the dielectric material of the dielectric layers alternates between the first dielectric material and the second dielectric material. For example, in one embodiment, dielectric materials of dielectric layers 52 are selected such that dielectric layers $52_1$ and $52_3$ have a high index of refraction while dielectric layer $52_2$ has a low index of refraction. This configuration is advantageous because the magnitude of the anomalies exhibited by light beams 64 and 66 are substantial and more readily detectable, thereby increasing the sensitivity of sensor 50.

As light beam 62 penetrates the dielectric film stack of sensor 50, a portion of light beam 62 is reflected at each dielectric layer 52. More specifically, as light beam 62 penetrates a given dielectric layer 52, a portion of the light is reflected at the surface of the next dielectric layer 52. As such, when light beam 62 is incident normal to the dielectric film stack, the total distance traveled within any given dielectric layer is approximately twice the thickness, t, of the dielectric layer, i.e., 2 t. In order to form the dielectric film stack as a dielectric mirror such that light beam 62 is substantially reflected from sensor 50 as light beam 66, each dielectric layer 52 is formed with an approximate thickness t defined by the following equation:

$$t = \frac{\lambda}{4n} + \frac{m*\lambda}{2n}$$

where $\lambda$ is the wavelength of light beam 62, n is the index of refraction of the dielectric layer being formed and m is any positive integer. For other angles of incidence, this equation is easily modified.

When each dielectric layer is formed according to the above equation, and m equals zero, the total distance traveled within a given dielectric layer is $\lambda/2$ n. This corresponds to a total "optical" distance traveled within each dielectric layer of one half of the wavelength of the light, $\lambda/2$, which corresponds to a retardation of 180°.

At the reflecting surface there is an additional 180° of retardation if the penetrated dielectric layer has a high index of refraction, n, and the next dielectric layer has a low index. Therefore, for each of these high index/low index interfaces, reflected light beam 66 undergoes a total retardation of 360° and returns to the surface of the penetrated dielectric layer 52 in phase with the portion of light beam 66 reflected from that surface. When the dielectric film stack is formed according to the above equation and dielectric layers 52 alternate between a high index and a low index, all the internally reflected light beam 66 are in phase, thereby causing constructive interference that results in substantial reflectivity. For example, according to this configuration, sensor 50 can be constructed to reflect at least 50%, or even at least 90%, of light beam 62. The dielectric film stack acts as a dielectric mirror when the dielectric layers are formed according to the above equation for any positive integer m. As m increases, the thickness t increases by $\lambda/2$ such that the total "optical" distance traveled within a dielectric layer increases by one full wavelength $\lambda$, thereby resulting in interference and substantial reflectivity of light beam 62.

In one embodiment, the dielectric material used for one set of the alternating dielectric layers, such as dielectric layers $52_1$ and $52_3$, is selected to have the highest index of refraction of any dielectric material that can be formed on sensor 50. For example, titanium dioxide, $TiO_2$, is a suitable dielectric material because it has an index of refraction equaling approximately 2.5. The dielectric material used for the other dielectric layers, such as dielectric layers 522, is selected to have the lowest index of refraction of any dielectric material that can be formed on sensor 50. For example, silicon dioxide, $SiO_2$, is a suitable dielectric material because it has an index of refraction equaling approximately 1.5. Selecting the dielectric materials for dielectric layers 52 as such provides a dielectric mirror having high reflectivity, often approaching 90%, for most angles yet exhibiting sharp attenuation at the resonance angles, often approaching 0% reflected light. Furthermore, a suitable dielectric material for dielectric layer 522 may have a corresponding index of refraction approaching 1.8. Similarly, a suitable dielectric material for dielectric layers $52_1$ and $52_3$ may have a corresponding index of refraction of at least 2.2. In addition, the magnitude of the exhibited anomaly increases as the number of dielectric layers increases; however, the magnitude of the angular shift tends to decrease. Therefore a balance between these two characteristics must be determined. Although other numbers of layers are acceptable, experiments suggest that five to fifteen dielectric layers provide good results with eleven layers working particularly well.

In order for the dielectric film stack of sensor 50 to operate as a dielectric mirror it is not necessary that the dielectric film stack be formed from two alternating dielectric layers. A dielectric layer mirror can also be constructed with dielectric layers having several different indices of refraction. In this case it is important that the thickness of each layer be described by the previous equation. In addition, each layer must be bounded by other layers that both have either a higher refractive index or a lower refractive index. For example, the dielectric film stack may be formed from three dielectric materials with indices $n_1$, $n_2$, $n_3$ where $n_1<n_2<n_3$. A suitable dielectric film stack formed from these materials could be constructed by following the sequence of dielectric indexes: $n_3,n_2,n_3,n_1,n_2,n_1,n_3,n_2,n_3$.

As described above, the dielectric film stack of sensor 50 can be constructed to operate as an anti-reflection dielectric film stack. Although there is no general equation that can be given for designing anti-reflection film stacks, an iterative approach using computer modeling may be used. Following this approach, one example of an antireflecting dielectric film stack is $TiO_2$, $SiO_2$ and $TiO_2$ deposited on a glass substrate for which the index of refraction of the $TiO_2$ layers is 2.5 and the index of refraction of the $SiO_2$ layer and the glass substrate is 1.5. In this configuration, the thickness of the $TiO_2$ layer against the substrate is 102 nm, the thickness of the $SiO_2$ layer is 120 nm, and the thickness of the outer $TiO_2$ layer is 114 nm. The reflected light intensity for light incident perpendicularly to the substrate at a wavelength of 635 nm is essentially zero.

Figure 4:
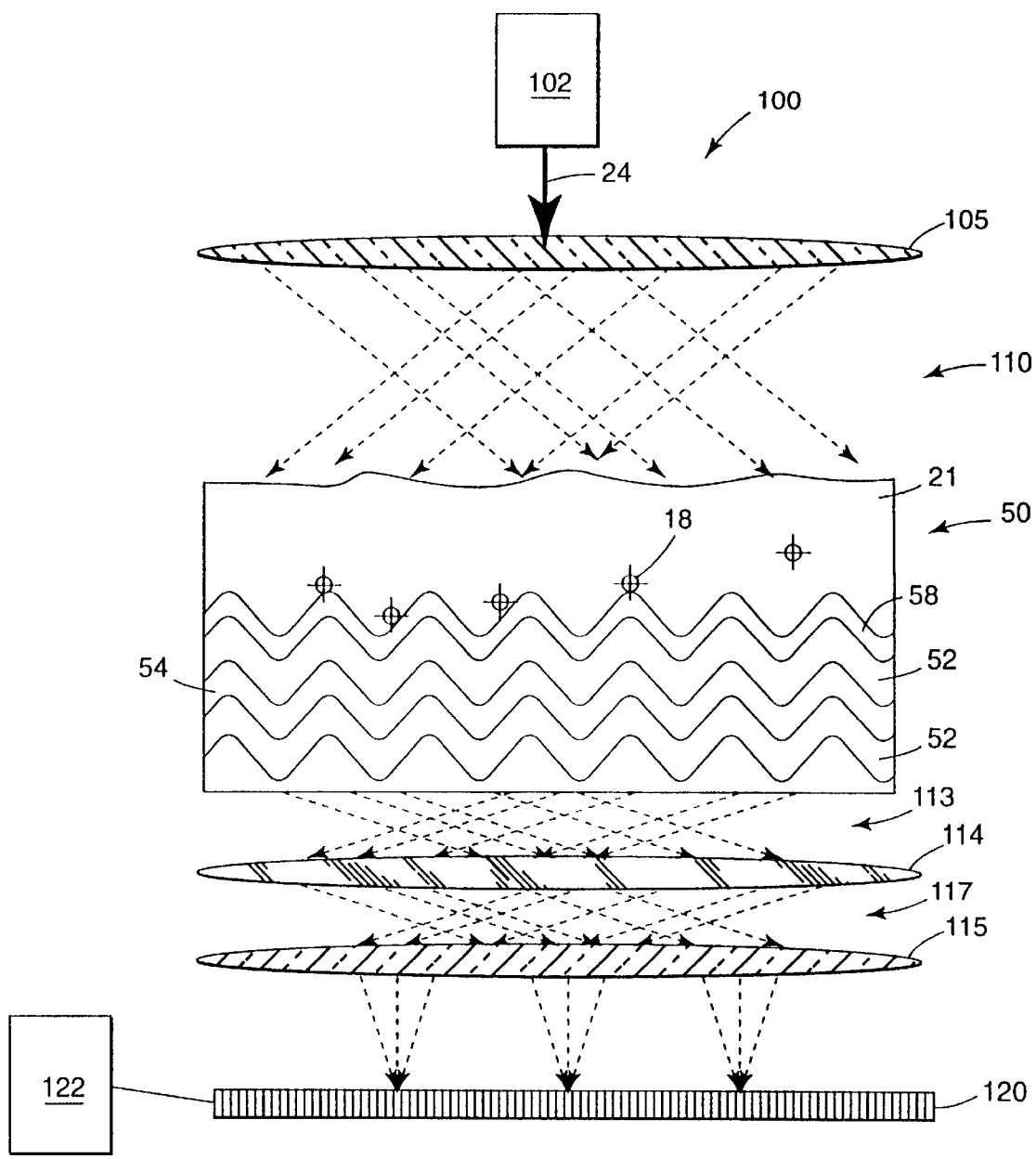
FIG. 4 is a schematic side view of one embodiment of a sensing system for assaying a substance in a sample by exposing a sensor having a dielectric film stack and detecting a shift in one or more resonance angles.

FIG. 4 illustrates one embodiment of a sensing system 100 incorporating the improved optical sensor 50 described above. Sensing system 100 includes a monochromatic light source 102, such as a laser, that produces light beam 24 incident upon diffuser 105. Other light sources are suitable including a monochromatic light bulb such as a mercury lamp, a filtered light emitting diode, a white light source coupled with a filter, etc. Diffuser 105 diffuses light beam 24 such that light 110 is incident upon sensor 50 at a variety of angles. In one embodiment, the sample includes material for diffusing the light beam incident upon the sensor such that a separate diffuser is not needed. Depending upon the angle of incidence and corresponding resonance angles of sensor 50, light 110 is transmitted through sample 21, sensor 50 and illuminates polarizer 114 that transmits polarized light beam 117 having a electric vector parallel or perpendicular to the grooves of the surface of sensor 50.

Lens 115 focuses polarized light 117 to a corresponding point along detector array 120. In other words, polarized light 117 enters lens 115 at a variety of angles and is focused along detector array 120 according to the angle. Detector array 120 outputs a signal that indicates corresponding intensities of the light focused along detector array 120. Based on the signal, controller 122 determines one or more resonance angles and calculates a measure of the targeted substance in the sample. This configuration is particularly advantageous in the sense that no moving parts are required. In one embodiment, controller 122 sounds an alarm when the calculated measure of targeted substance 18 exceeds a predetermined threshold. After sensing is complete, sensor 50 may be disposed or may be washed and reused.

Several embodiments of an optical assaying method and apparatus have been described. In one aspect, the present invention is an optical sensor having dielectric film stack that includes a plurality of dielectric layers. Each dielectric layer comprises a dielectric material selected from a first dielectric material having a first index of refraction and a second dielectric material having a second index of refraction. In one embodiment, the dielectric film stack is formed such that the dielectric material of the dielectric layers alternates between the first dielectric material and the second dielectric material. The dielectric film stack is either formed as a dielectric mirror such that light incident upon the sensor reflects from the sensor or as an anti-reflection film stack such that light incident upon the light beam propagates through the sensor.

The inventive sensor is easily manufactured such that the resonance angles can easily be tuned yet overcomes the limitations of grating-based SPR sensors. More specifically, the inventive sensor uses a dielectric film stack instead of a thin metal film. The inventive sensor exhibits a resonance that is comparable in magnitude with resonances commonly exhibited by conventional SPR sensors. However, unlike grating-based SPR sensors, a sample may be assayed by reflectance from the substrate side without propagating light through the sample. In addition, the sensor allows a sample to be assayed with transmitted light. One advantage of assaying with transmitted light is the ability to use a diffused light source. In addition, because the sensor does not rely on the use of conductive metals, the sensor enables sharp resonances at shorter wavelengths than conventional SPR sensors.

We claim:

1. A sensor for optically assaying a substance in a sample comprising:
   a substrate having a grooved surface; and
   a dielectric film stack formed outwardly from the substrate, wherein the dielectric film stack includes a plurality of dielectric layers, and further wherein for at least one angle of incidence the dielectric layers operate as a waveguide for light incident upon the sensor, and the dielectric film stack is formed as a dielectric mirror such that the light incident upon the sensor reflects from the sensor when the dielectric film stack is not operating as a waveguide.

2. The sensor of claim 1, wherein at least two of the dielectric layers comprise a dielectric material selected from a first dielectric material and a second dielectric material, wherein the first dielectric material has a first index of refraction and the second dielectric material has a second index of refraction.

3. The sensor of claim 2, wherein the dielectric film stack is formed such that the dielectric material of the dielectric layers alternates between die first dielectric material and the second dielectric material.

4. The sensor of claim 2, wherein die first index of refraction is substantially no greater than 1.8, and further wherein the second index of refraction is substantially no less than 2.2.

5. The sensor of claim 2, wherein the first dielectric material is silicon dioxide and the second dielectric material is titanium dioxide.

6. The sensor of claim 1, wherein the dielectric film stack is formed such that when the dielectric film stack operates as a waveguide the reflected light exhibits an attenuation of substantially at least 50%.

7. The sensor of claim 1, wherein die dielectric film stack is formed such that when the dielectric film stack operates as a waveguide the reflected light exhibits an attenuation of substantially at least 90%.

8. The sensor of claim 1, further comprising a sensitizing layer formed outwardly from the dielectric film stack, wherein the sensitizing layer interacts with the substance in the sample.

9. A sensor for optically assaying a substance in a sample comprising:

a substrate having a grooved surface; and a dielectric film stack formed outwardly from the substrate, wherein the dielectric film stack Includes a plurality of dielectric layers, and further wherein for at least one angle of incidence the dielectric layers operate as a waveguide for light incident upon the sensor, and the dielectric film stack is formed as an anti-reflection film stack such that the Incident light passes through the sensor when the dielectric film stack is not operating as a waveguide.

10. The sensor of claim 9, wherein the dielectric film stack is formed such that when the dielectric film stack operates as a waveguide the transmitted light exhibits an attenuation of substantially at least 50%.

11. The sensor of claim 9, wherein the dielectric film stack is formed such that when the dielectric film stack operates as a waveguide the transmitted light exhibits an attenuation of substantially at least 90%.

12. The sensor of claim 9, wherein at least two of the dielectric layers comprise a dielectric material selected from a first dielectric material and a second dielectric material, wherein the first dielectric material has a first index of refraction and the second dielectric material has a second index of refraction.

13. The sensor of claim 12, wherein the dielectric film stack is formed such that the dielectric material of the dielectric layers alternates between the first dielectric material and the second dielectric material.

14. The sensor of claim 12, wherein the first index of refraction is substantially no greater than 1.8, and further wherein the second index of refraction is substantially no less than 2.2.

15. The sensor of claim 12, wherein the first dielectric material is silicon dioxide and the second dielectric material is titanium dioxide.

16. The sensor of claim 9, further comprising a sensitizing layer formed outwardly from the dielectric film stack, wherein the sensitizing layer interacts with the substance in the sample.

* * * * *